United States Patent
Cosmescu

(10) Patent No.: US 10,512,500 B2
(45) Date of Patent: Dec. 24, 2019

(54) ULTRAPOLAR TELESCOPIC ELECTROSURGERY PENCIL WITH ARGON BEAM CAPABILITY

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 363 days.

(21) Appl. No.: 15/649,429

(22) Filed: Jul. 13, 2017

(65) Prior Publication Data

US 2018/0092684 A1  Apr. 5, 2018

Related U.S. Application Data

(60) Provisional application No. 62/362,873, filed on Jul. 15, 2016, provisional application No. 62/362,968, filed on Jul. 15, 2016.

(51) Int. Cl.

| | | |
|---|---|---|
| *A61B 18/14* | (2006.01) | |
| *A61B 18/04* | (2006.01) | |
| *A61M 13/00* | (2006.01) | |
| A61B 17/00 | (2006.01) | |
| A61B 18/00 | (2006.01) | |
| A61B 18/12 | (2006.01) | |

(52) U.S. Cl.
CPC ........ *A61B 18/1402* (2013.01); *A61B 18/042* (2013.01); *A61M 13/003* (2013.01); *A61B 2017/00991* (2013.01); *A61B 2018/00077* (2013.01); *A61B 2018/00083* (2013.01); *A61B 2018/00589* (2013.01); *A61B 2018/00601* (2013.01); *A61B 2018/00607* (2013.01); *A61B 2018/1246* (2013.01); *A61B 2018/1412* (2013.01); *A61B 2218/005* (2013.01)

(58) Field of Classification Search
CPC ... A61B 18/042; A61B 18/14; A61B 18/1402; A61B 2018/00077; A61B 2018/00083; A61B 2018/00589; A61B 2018/00601; A61B 2018/00607; A61B 2018/1246; A61B 2018/1412; A61B 2017/00991
See application file for complete search history.

(56) References Cited

U.S. PATENT DOCUMENTS

| | | | |
|---|---|---|---|
| 4,674,498 A | 6/1987 | Stasz | |
| 5,256,138 A | 10/1993 | Burek et al. | |
| 5,281,216 A | 1/1994 | Klicek | |
| 5,693,044 A * | 12/1997 | Cosmescu | ............ A61B 18/042 604/35 |
| 6,355,034 B2 * | 3/2002 | Cosmescu | .......... A61B 18/1402 606/41 |
| 7,815,638 B2 * | 10/2010 | Farin | .................... A61B 18/042 606/41 |
| 2013/0110108 A1 | 5/2013 | Davison et al. | |

FOREIGN PATENT DOCUMENTS

| | | |
|---|---|---|
| WO | 2000/028908 A1 | 5/2000 |
| WO | 2014/138366 A1 | 9/2014 |

* cited by examiner

*Primary Examiner* — Michael F Peffley
(74) *Attorney, Agent, or Firm* — Zeman-Mullen & Ford, LLP

(57) ABSTRACT

An ultrapolar telescopic electrosurgery pencil with argon beam capability that is capable of using monopolar energy in a bipolar mode for cutting and coagulation and also using ionized gas for cutting and coagulation.

13 Claims, 3 Drawing Sheets

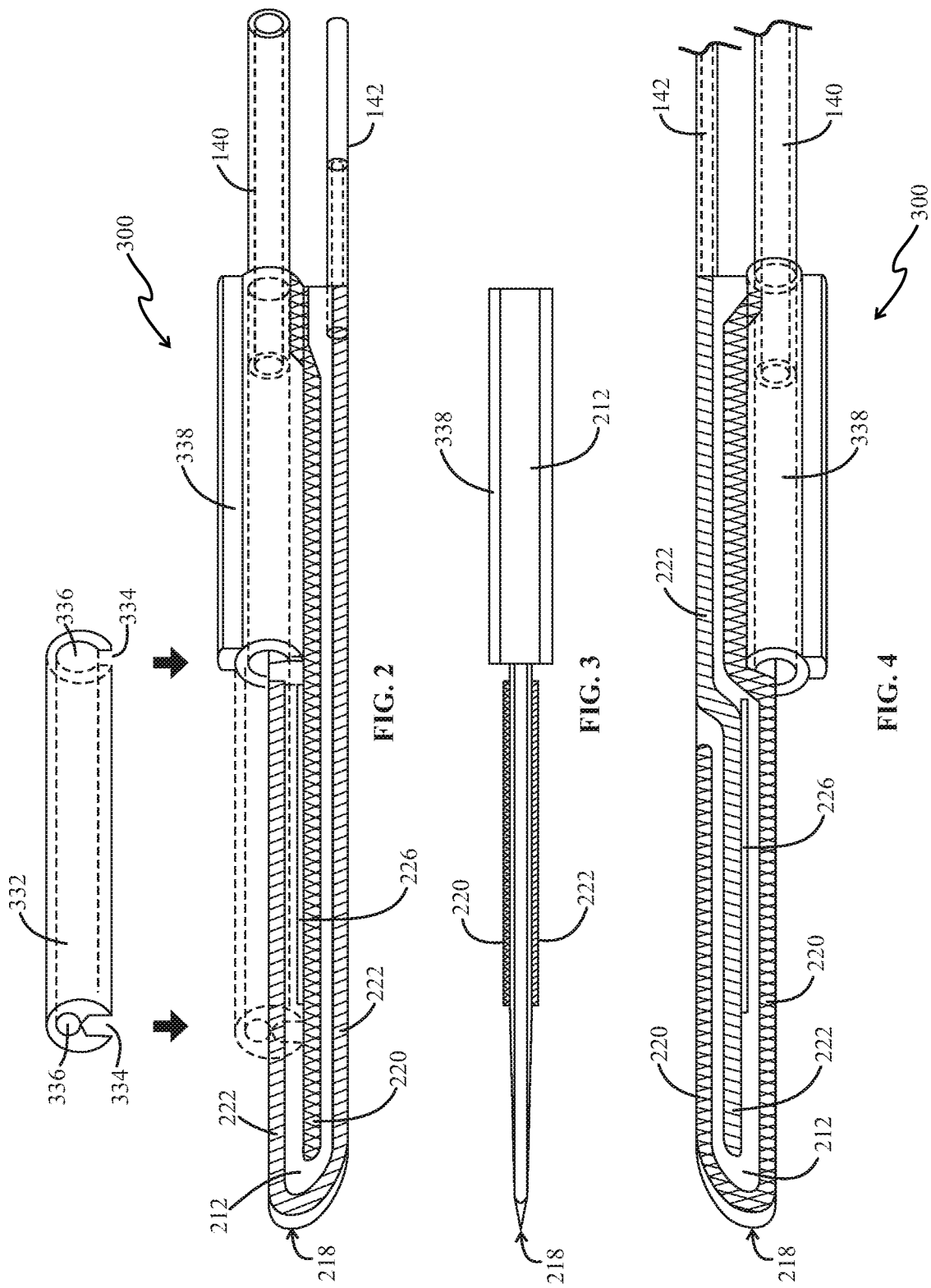

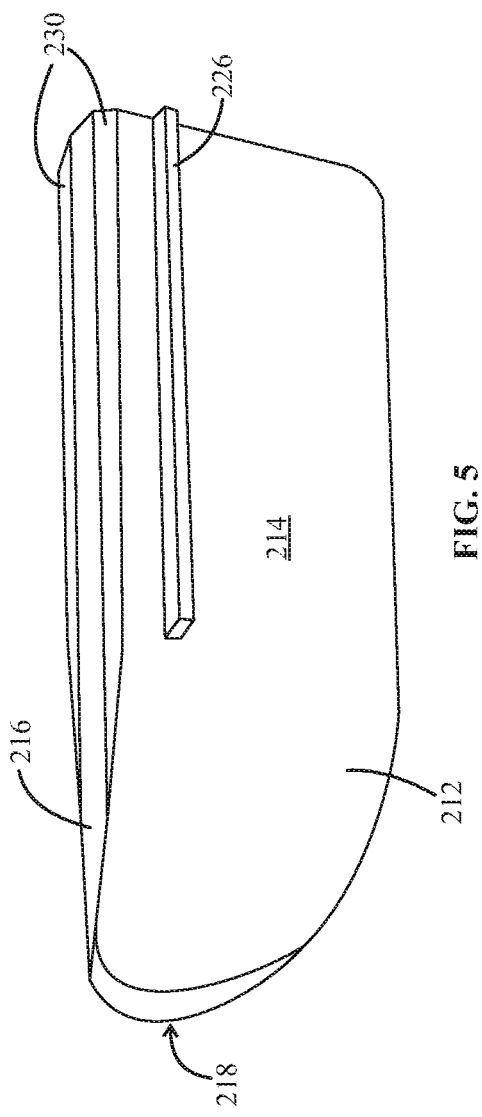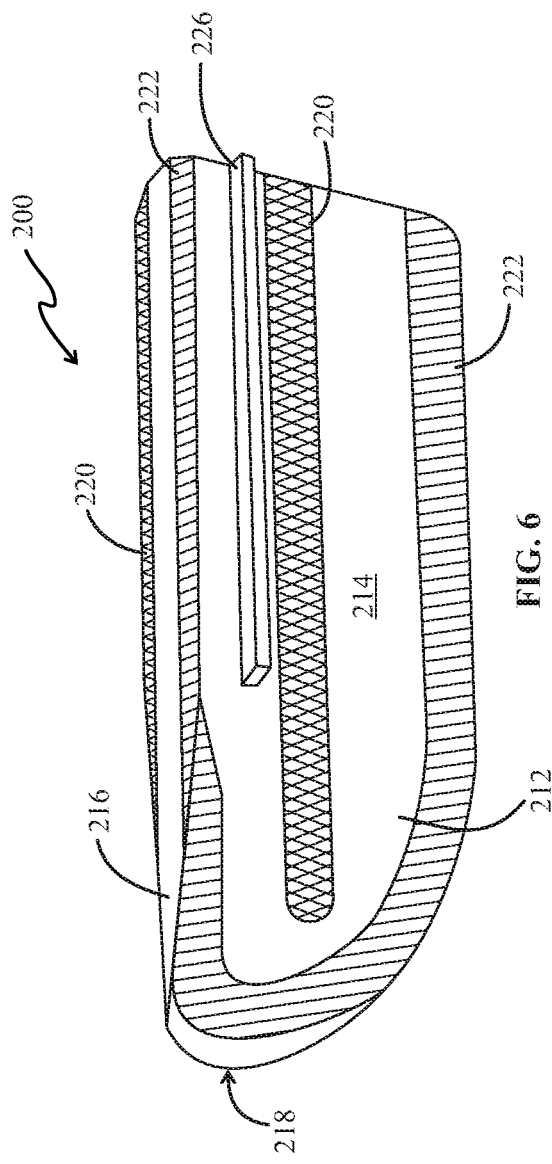
FIG. 5
FIG. 6

ULTRAPOLAR TELESCOPIC ELECTROSURGERY PENCIL WITH ARGON BEAM CAPABILITY

CROSS-REFERENCE TO RELATED APPLICATIONS

This application relates to provisional patent application having Ser. No. 62/362,873 entitled "Ultrapolar Electrosurgery Blade Assembly And Ultrapolar Electrosurgery Pencil With Argon Beam Capability," filed Jul. 15, 2016, and provisional patent application having Ser. No. 62/362,968 entitled "Ultrapolar Telescopic Electrosurgery Pencil Having Argon Beam Capability," filed Jul. 15, 2016, both of which are herein incorporated by reference in their entireties.

FIELD OF INVENTION

The present invention is generally directed to an ultrapolar telescopic electrosurgery pencil with argon beam capability which is capable of using monpolar energy in a bipolar mode for cutting and coagulation and also capable of using an ionized gas for cutting and coagulation.

BACKGROUND OF THE INVENTION

Electrosurgery uses an RF electrosurgical generator (also known as an electrosurgical unit or ESU) and a handpiece with an electrode to provide high frequency, alternating radio frequency (RF) current input at various voltages to cut or coagulate biological tissue. The handpiece may be a monopolar instrument with one electrode or a bipolar instrument with two electrodes. When using a monopolar instrument, a return electrode pad is attached to the patient and the high frequency electrical current flows from the generator, to the monopolar instrument, through the patient to the patient return electrode pad, and back to the generator. Monopolar electrosurgery is commonly used due to its versatility and effectiveness. However, the excessive heat generated with monopolar electrosurgery can cause excessive tissue damage and necrosis of the tissue because the return electrode positioned on the back of the patient causes high voltage and high RF energy to pass through the patient.

In bipolar electrosurgery, active output and patient return functions both occur at the surgery site because both the active and return electrodes are contained in the bipolar instrument. Therefore, the path of the electrical current is confined to the biological tissue located between the active and return electrodes. Although bipolar electrosurgery enables the use of lower voltages and less energy than monopolar electrosurgery and thereby reduces or eliminates the likelihood of tissue damage and sparking associated with monopolar electrosurgery, it has limited ability to cut and coagulate large bleeding areas.

It is also common to use argon beam coagulators during electrosurgery. In argon beam coagulation (ABC), current is applied to tissue by a directed beam of ionized argon gas which causes a uniform and shallow coagulation surface thereby stopping blood loss. However, argon beam enhanced cutting may also be performed using application of an ionized argon gas.

At present, electrosurgery is often the best method for cutting and argon beam coagulation is often the best method for cessation of bleeding during surgery. Surgeons typically need to switch between argon beam coagulation and electrosurgery modes depending on what is happening during the surgery and what they need to achieve at a particular point in the surgery such as cutting, or making incisions in tissue, or stopping the bleeding at the surgical site.

However, since surgical tools and devices currently available to surgeons require switching between these two methods during the surgical procedure, there is a need for a surgical device or tool that enables a surgeon or user to utilize the best methods used for cutting and cessation of bleeding at the surgical site both separately and at the same time, or simultaneously, in addition to being able to use them separately. A telescopic electrosurgery pencil with argon beam capability that includes an electrode blade assembly with argon beam capability can provide a user or surgeon with safe, efficient, effective, and flexible ways to both cut and coagulate tissue during electrosurgery. In addition, the telescoping ability of an ultrapolar telescopic electrosurgery pencil can enable a user or surgeon to adjust the length of the ultrapolar electrosurgery pencil to better accommodate accessing different surgical sites.

SUMMARY OF THE INVENTION

The present invention is directed to a telescopic ultrapolar electrosurgery pencil with argon beam capability that is capable of using monopolar energy in a bipolar mode for cutting and coagulation using an electrosurgery blade and also using ionized gas for cutting and coagulation thereby providing a user or surgeon with a variety of ways to perform cutting and/or coagulation of tissue during an operative procedure.

In one exemplary embodiment, the ultrapolar electrosurgery blade assembly contained within the ultrapolar telescopic electrosurgery pencil of the present invention includes an ultrapolar electrosurgery blade having a non-conductive blade with opposing planar sides, a narrow elongated top, a sharp cutting end, and an opposite non-cutting end, and both an active electrode or active contact and a return electrode or return contact (note that the terms electrode and contact are used interchangeably throughout this specification) located on each of the opposing planar sides of the non-conductive blade, and a non-conductive hollow tubular member positioned over the narrow elongated top of the non-conductive blade so that the non-conductive hollow tubular member covers at least a portion of an active electrode/contact on one of the opposing planar sides of the non-conductive blade and at least a portion of a return electrode/contact on the other opposing planar side of the non-conductive blade. This enables a gas supplied to the non-conductive hollow tubular member to be ionized as it comes into contact with the active and return electrodes/contacts contained within the non-conductive hollow tubular member thereby enabling both cutting and coagulation of tissue without high voltage and high RF energy passing through the patient.

In another exemplary embodiment of the ultrapolar electrosurgery blade assembly contained within the ultrapolar telescopic electrosurgery pencil of the present invention, a second non-conductive hollow tubular member may also be included as part of the ultrapolar electrosurgery blade assembly by positioning it adjacent to the previously described non-conductive hollow tubular member that is positioned over at least a portion of both active and return contacts located on opposite sides of the electrosurgery blade. In this embodiment, the second non-conductive hollow tubular member may also be positioned and fixed over the electrosurgery blade (but not necessarily positioned over both active and return contacts on the electrosurgery blade)

and the previously described non-conductive hollow tubular member may be supported in its position over at least a portion of the active and return contacts of the electrosurgery blade by seating it on a non-conductive shelf support located on the electrosurgery blade. This enables the non-conductive hollow tubular member that is positioned over at least a portion of active and return contacts of the electrosurgery blade to be changeable/replaceable if desired. Alternatively, the non-conductive hollow tubular member that is positioned over at least a portion of active and return contacts of the electrosurgery blade may also be permanently attached to the second non-conductive hollow tubular member and/or the non-conductive shelf support. The non-conductive hollow tubular member may include a slot which fits over the electrosurgery blade and an opening located above the slot through which an ionized gas can project after coming into contact with the active and return contacts of the electrosurgery blade contained within the non-conductive hollow tubular member.

An exemplary embodiment of the ultrapolar telescopic electrosurgery pencil with argon beam capability of the present invention includes a handpiece member with a channel having first and second ends; a first conductive hollow tube contained within the channel; a second conductive hollow tube contained within the channel; a hollow telescopic member having first and second ends where the second end of the hollow telescopic member is contained within the handpiece member; a third conductive hollow tube having a smaller diameter than the first conductive hollow tube where the third conductive hollow tube is contained within the hollow telescopic member and at least a portion of the first conductive hollow tube; a conductive cylindrical member contained within the hollow telescopic member and at least a portion of the second conductive hollow tube; an ultrapolar electrosurgery blade positioned within the first end of the hollow telescopic member where the ultrapolar electrosurgery blade includes a non-conductive blade having opposing planar sides, a sharp cutting end, and both an active contact and a return contact on each of the opposing planar sides of the non-conductive blade where the active contacts are connected to the third conductive hollow tube and the return contacts are connected to the conductive cylindrical member; and a non-conductive hollow tubular member positioned on the ultrapolar electrosurgery blade so that it covers at least a portion of an active contact on one opposing planar side of the non-conductive blade and at least a portion of a return contact on the other opposing planar side of the non-conductive blade.

The channel within the handpiece member and the interior of the hollow telescopic member together function as a smoke evacuation channel for evacuating smoke and/or debris away from the sharp cutting end of the non-conductive blade where cutting and/or coagulation are taking place during operative procedures. The ultrapolar telescopic electrosurgery pencil with argon beam capability may also include a rotating/swivel member connected to the second end of the handpiece to alleviate drag on the end of the ultrapolar telescopic electrosurgery pencil and kinking of a suction tube when a suction tube is attached to the end of the ultrapolar telescopic electrosurgery pencil to evacuate smoke and/or debris from the smoke evacuation channel.

The ultrapolar telescopic electrosurgery pencil with argon beam capability of the present invention may also include additional elements including, but not limited to, at least one support member for retaining the first conductive hollow tube and the second conductive hollow tube within the channel of the handpiece, at least one support member for retaining the third conductive hollow tube and the conductive cylindrical member within the hollow telescopic member, a second non-conductive hollow tubular member positioned between, and connected to, the non-conductive hollow tubular member and the third conductive hollow tube, and a non-conductive shelf support for supporting the non-conductive hollow tubular member when positioned on the ultrapolar electrosurgery blade.

The non-conductive hollow tubular member and the non-conductive blade may each comprise a ceramic. The non-conductive hollow tubular member may include a slot which fits over at least a portion of a top of the ultrapolar electrosurgery blade and an opening located above the slot on each end of the non-conductive tubular member. Further, the hollow non-conductive tubular member may be positioned outside of the first end of the hollow telescopic member. In addition, one or both of the second conductive hollow tube and the first conductive hollow tube may be insulated about their exterior outer surfaces.

The exemplary embodiments of the ultrapolar telescopic electrosurgery pencil with argon beam capability of the present invention enable a user or surgeon to perform cutting with the sharp non-conductive tip of the electrosurgery blade, cutting with the active and return electrodes/contacts of the electrosurgery blade, coagulating large areas of biological tissue by placing the electrosurgery blade on either of its sides where both active and return electrodes/contacts are located, and cutting and/or coagulating tissue using ionized gas that projects from the non-conductive hollow tubular shaped member that is positioned over active and return electrodes/contacts contained on the electrosurgery blade. A particularly new and innovative feature of the ultrapolar telescopic electrosurgery pencil with argon beam capability of the present invention is the ability of a user or surgeon to simultaneously cut tissue with the sharp non-conductive tip of the electrosurgery blade while coagulating tissue using ionized gas that projects from the non-conductive hollow tubular shaped member that is positioned over active and return electrodes/contacts contained on the electrosurgery blade. The ultrapolar telescopic electrosurgery pencil with argon beam capability of the present invention provides a user or surgeon with safe, efficient, effective, and flexible ways to both cut and coagulate tissue during electrosurgery. The ultrapolar telescopic electrosurgery pencil with argon beam capability of the present invention is much safer for the patient than other electrosurgery instruments and methods due to the fact that high voltage and high RF energy do not need to pass through the patient during electrosurgery. In addition, the telescoping ability of the ultrapolar telescopic electrosurgery pencil with argon beam capability of the present invention enables a user or surgeon to adjust the length of the ultrapolar pencil to better accommodate accessing different surgical sites.

BRIEF DESCRIPTION OF THE DRAWINGS

FIG. 2 is a partial exploded perspective view of an exemplary embodiment of the ultrapolar electrosurgery blade assembly contained in the ultrapolar telescopic electrosurgery pencil depicted in FIG. 1 and the third conductive tube and conductive cylindrical member of the ultrapolar telescopic electrosurgery pencil depicted in FIG. 1 in order to show how the ultrapolar electrosurgery blade assembly is connected to the interior components of the ultrapolar telescopic electrosurgery pencil;

FIG. 3 is a top plan view of the exemplary embodiment of the ultrapolar electrosurgery blade assembly shown in FIG. 2 without the non-conductive hollow tubular member of the ultrapolar electrosurgery blade assembly and without the third conductive hollow tube of the ultrapolar telescopic electrosurgery pencil;

FIG. 4 is a perspective view of the exemplary embodiment of the ultrapolar electrosurgery blade assembly, third conductive tube, and conductive cylindrical member of the ultrapolar telescopic electrosurgery pencil depicted in FIG. 2 shown rotated 180 degrees to show the active and return contacts/electrodes located on the opposite side of the ultrapolar electrosurgery blade;

FIG. 5 is a partial perspective view showing the shape of the non-conductive blade portion of the ultrapolar electrosurgery blade depicted in FIGS. 1-4 and FIG. 6; and FIG. 6 is a partial perspective view of the ultrapolar electrosurgery blade depicted in FIGS. 1-5 shown with its active and return contacts.

DETAILED DESCRIPTION OF EXEMPLARY EMBODIMENTS

Figure 1:
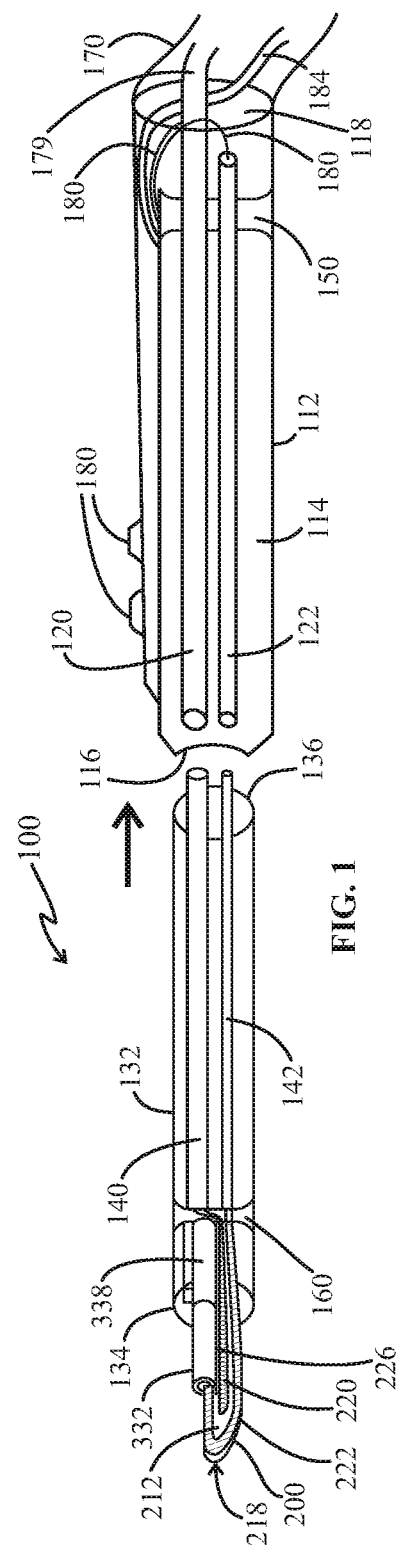
FIG. 1 is a perspective view of an exemplary embodiment of an ultrapolar telescopic electrosurgery pencil with argon beam capability of the present invention shown with the handpiece and hollow telescopic members unconnected and sides of the handpiece and hollow telescopic members removed to show the interior elements of the electrosurgery pencil.

The ultrapolar telescopic electrosurgery pencil with argon beam capability of the present invention provides a user or surgeon with a variety of ways to perform cutting and/or coagulation of tissue during an operative procedure. The ultrapolar telescopic electrosurgery pencil with argon beam capability can use monopolar energy in a bipolar mode for cutting and coagulation using an electrosurgery blade and can also use an ionized gas for cutting and coagulation. In addition, a channel within the ultrapolar telescopic electrosurgery pencil with argon beam capability enables smoke and/or debris to be evacuated away from the surgical site while using the electrosurgery blade and/or ionized gas for cutting and/or coagulation. Further, the telescoping ability of the ultrapolar telescopic electrosurgery pencil with argon beam capability of the present invention enables a user or surgeon to adjust the length of the ultrapolar pencil to better accommodate accessing different surgical sites.

It will be understood by those skilled in the art that the active and return electrodes/contacts as depicted in all of the drawing figures may be reversed—i.e. the contacts shown as active contacts could be return contacts and the contacts shown as return contacts could be active contacts since both opposing planar sides of the non-conductive electrosurgery blade have both active and return contacts that mimic the configuration of one another. Reversing the types of electrodes/contacts would still result in the ultrapolar telescopic electrosurgery pencil with argon beam capability having the same functional features and advantages. The terms "electrode" and "contact" are meant to be used interchangeably throughout the specification.

FIG. 1 is a perspective view of an exemplary embodiment of an ultrapolar telescopic electrosurgery pencil with argon beam capability 100 of the present invention shown with the handpiece and hollow telescopic members unconnected and sides of the handpiece and hollow telescopic members removed to show the interior elements of the electrosurgery pencil. The ultrapolar telescopic electrosurgery pencil with argon beam capability 100 includes a handpiece member 112 with a channel 114 having first and second ends 116, 118, a first conductive hollow tube 120 contained within the channel 114, a second conductive hollow tube 122 contained within the channel 114, a hollow telescopic member 132 having first and second ends 134, 136 wherein the second end 136 is contained within the handpiece member 112, a third conductive hollow tube 140 having a smaller diameter than the first conductive hollow tube 120 and contained within the hollow telescopic member 132 and at least a portion of the first conductive hollow tube 120, a conductive cylindrical member 142 contained within the hollow telescopic member 132 and at least a portion of the second conductive hollow tube 122, and an ultrapolar electrosurgery blade 200 positioned within the first end 134 of the hollow telescopic member 132. The ultrapolar electrosurgery blade 200 includes a non-conductive blade 212 having opposing planar sides 214, a sharp cutting end 218, and both an active contact 220 and a return contact 222 located on each of the opposing planar sides 214 of the non-conductive blade 212 where the active contacts 220 are connected to the third conductive hollow tube 132 and the return contacts 222 are connected to the conductive cylindrical member 142. Further, a non-conductive hollow tubular member 332 is positioned on the ultrapolar electrosurgery blade 200 such that it covers at least a portion of an active contact 220 on one opposing planar side 214 of the non-conductive blade 212 and at least a portion of a return contact 222 on the other opposing planar side 214 of the non-conductive blade 212. A second non-conductive hollow tubular member 338 may also be positioned on ultrapolar electrosurgery blade 200 such that is lies adjacent to, and connects with non-conductive hollow tubular member 332. A non-conductive shelf support 226 may be included on the non-conductive blade 212 for supporting the non-conductive hollow tubular member 332 when positioned on the ultrapolar electrosurgery blade 200.

The ultrapolar electrosurgery blade 200 and the non-conductive hollow tubular member 332 (and second non-conductive tubular member 338 if also included) together form an ultrapolar electrosurgery blade assembly having argon beam capability 300 which is further described in detail with respect to FIGS. 2-4. In addition, exemplary embodiments of the ultrapolar electrosurgery blade assembly having argon beam capability 300 are also described in provisional patent application having Ser. No. 62/362,873 and its related utility patent application having Ser. No. 15/648,553, both of which are herein incorporated by reference in their entireties.

The ultrapolar telescopic electrosurgery pencil with argon beam capability 100 may also include at least one support member 150 for retaining the first conductive hollow tube 120 and the second hollow conductive tube 122 within the channel 114 of the handpiece member 122. The ultrapolar telescopic electrosurgery pencil with argon beam capability 100 may also include at least one support member 160 for retaining the third conductive hollow tube 140 and the conductive cylindrical member 142 within the hollow telescopic member 132.

The ultrapolar telescopic electrosurgery pencil with argon beam capability 100 may further include a rotating/swivel member 170 connected to the second end 118 of handpiece member 112 to avoid drag on the end of the ultrapolar telescopic electrosurgery pencil 100 when operating and to facilitate maneuvering of the ultrapolar telescopic electrosurgery pencil 100 when a vacuum is attached to it for the evacuation of smoke and/or debris. In addition, the ultrapolar electrosurgery blade assembly having argon beam capability 300 is positioned within the first end 134 of the hollow telescopic member 132 so that non-conductive hollow tube member 332 is located outside of the first end 134 of the hollow telescopic member 132. Still further, first conductive hollow tube 120 and second conductive hollow tube 122 contained within handpiece member 112 may have an insulator on their outer surfaces.

FIG. 6 is a partial perspective view of the ultrapolar electrosurgery blade depicted in FIGS. 1-5 shown with its active and return contacts which comprises part of the ultrapolar telescopic electrosurgery pencil with argon beam capability 100 of the present invention. Ultrapolar electrosurgery blade 200 includes a non-conductive blade 212 having opposing planar sides 214, a narrow elongated top 216, a sharp cutting end 218 and an opposite non-cutting end (not shown due to the partial view of the blade). Ultrapolar electrosurgery blade 200 also includes both an active electrode 220 and a return electrode 222 located on each of the opposing planar sides 214 of the non-conductive blade 212. Portions 224 of active electrode 220 and return electrode 222 that are located adjacent to the narrow elongated top 216 of non-conductive blade 212 reside on top side portions 230 of non-conductive blade 212 that project outward and downward from the narrow elongated top 216. The ultrapolar electrosurgery blade 200 may also include a non-conductive shelf support 226 for supporting the non-conductive hollow tubular member 332 that comprises part of the electrosurgery blade assembly with argon beam capability 300 shown and described with reference to FIGS. 2-4.

FIG. 5 is a partial perspective view showing the shape of the non-conductive blade portion 212 of the ultrapolar electrosurgery blade 200 depicted in FIGS. 1-4 and FIG. 6. Non-conductive blade 212 includes opposing planar sides 214, a narrow elongated top 216, a sharp cutting end 218 and an opposite non-cutting end (not shown due to the partial view of the blade). Top side portions 230 of non-conductive blade 212 projects outward and downward from the narrow elongated top 216 and into opposing planar sides 214 of the non-conductive blade 212. Non-conductive blade 212 may also include a non-conductive shelf support 226 for supporting the non-conductive hollow tubular member 332 that comprises part of the electrosurgery blade assembly with argon beam capability 300.

FIG. 2 is a partial exploded perspective view of an exemplary embodiment of the ultrapolar electrosurgery blade assembly 300 contained in the ultrapolar telescopic electrosurgery pencil 100 depicted in FIG. 1 and the third conductive hollow tube 140 and conductive cylindrical member 142 of the ultrapolar telescopic electrosurgery pencil 100 depicted in FIG. 1 in order to show how the ultrapolar electrosurgery blade assembly 300 is connected to the interior components of the ultrapolar telescopic electrosurgery pencil 100. First non-conductive hollow tubular member 332 has a slot 334 which fits over the narrow elongated top 216 of the non-conductive blade 212 such that the non-conductive hollow tubular member 332 covers at least a portion of an active electrode 220 on one opposing planar side 214 of the non-conductive blade 212 and at least a portion of a return electrode 222 on the other opposing planar side 214 of the non-conductive blade 212. The non-conductive hollow tubular member 332 further includes an opening 336 located above the slot 334 on each end of the non-conductive hollow tubular member 332. This enables a gas supplied to the non-conductive hollow tubular member 332 to be ionized as it comes into contact with portions of the active and return electrodes contained within the non-conductive hollow tubular member 332 and the ionized gas is then projected through the opening 336 of the non-conductive hollow tubular member 332 that is located closest to the sharp cutting end 218 of the ultrapolar electrosurgery blade 200.

A second non-conductive hollow tubular member 338 may be positioned over the narrow elongated top 216 of the non-conductive blade 212 adjacent to the first non-conductive hollow tubular member 332 but does not cover any portion of the return electrodes/contacts 222. However, second non-conductive hollow tubular member 338 may cover a portion of active electrodes/contacts 220 that are located near the non-cutting end of the non-conductive blade 212. The first non-conductive hollow tubular member 332 can be seated on the non-conductive shelf support 226 of the ultrapolar electrosurgery blade 200 and the first non-conductive hollow tubular member 332 may be changeable/replaceable. Alternatively, the first non-conductive hollow tubular member 332 may be permanently attached to the second non-conductive hollow tubular member 338 and/or the non-conductive shelf support 226.

The ultrapolar electrosurgery blade assembly 300 is connected to elements contained within the hollow telescopic member 132 of the ultrapolar telescopic electrosurgery pencil 100. More specifically, one end of third conductive hollow tube 140 of the ultrapolar telescopic electrosurgery pencil 100 is inserted within, and connected to, the second non-conductive hollow tubular member 338 of the ultrapolar electrosurgery blade assembly 300 and one end of conductive cylindrical member 142 of the ultrapolar telescopic electrosurgery pencil 100 is connected to the return electrodes/contacts 222 located at the non-cutting end of the ultrapolar electrosurgery blade 200 of the ultrapolar electrosurgery blade assembly 300.

FIG. 3 is a top plan view of the exemplary embodiment of the ultrapolar electrosurgery blade assembly 300 shown in FIG. 2 without the non-conductive hollow tubular member 336 of the ultrapolar electrosurgery blade assembly 300 and without the third conductive hollow tube 140 of the ultrapolar telescopic electrosurgery pencil 100.

FIG. 4 is a perspective view of the exemplary embodiment of the ultrapolar electrosurgery blade assembly 300, third conductive tube 140, and conductive cylindrical member 142 of the ultrapolar telescopic electrosurgery pencil 100 depicted in FIG. 2 shown rotated 180 degrees to show the active and return contacts/electrodes located on the opposite side of the ultrapolar electrosurgery blade 200. As shown in FIGS. 2 and 4, when the first non-conductive hollow tubular member 332 is seated over the narrow elongated top 216 of ultrapolar electrosurgery blade 200, the first non-conductive hollow tubular member 332 will cover a portion of return electrode/contact 222 on one opposing planar side 214 of non-conductive blade 212 (See FIG. 2) and a portion of active electrode/contact 220 on the other opposing planar side 214 of non-conductive blade 212 (See FIG. 4). The non-conductive blade 212 and the first non-conductive hollow tubular member 332 may each comprise a ceramic material. The second non-conductive hollow tubular member 338 may also comprise a ceramic material.

One exemplary embodiment of the ultrapolar telescopic electrosurgery pencil 100 of the present invention may not include the second non-conductive hollow tubular member 338 of the ultrapolar electrosurgery blade assembly 300. In this embodiment, the non-conductive hollow tubular member 332 would be longer in length and would extend to the non-cutting end of the ultrapolar electrosurgery blade 200. In connecting the ultrapolar electrosurgery blade assembly 300 to elements contained within the hollow telescopic member 132 of the ultrapolar telescopic electrosurgery pencil 100 in this embodiment, one end of third conductive hollow tube 140 of the ultrapolar telescopic electrosurgery pencil 100 is inserted within, and connected to, the non-conductive hollow tubular member 332 of the ultrapolar electrosurgery blade assembly 300 and one end of conductive cylindrical member 142 of the ultrapolar telescopic electrosurgery pencil 100 is connected to the return electrodes/contacts 222 located at the non-cutting end of the ultrapolar electrosurgery blade 200 of the ultrapolar electrosurgery blade assembly 300.

Turning back to the exemplary embodiment of the ultrapolar telescopic electrosurgery pencil shown in FIG. 1, a supply of gas through tubing 179 is connected to first conductive hollow tube 120 and the gas travels through first conductive tube 120, third conductive tube 140, into second non-conductive tubular member 338 and through non-conductive tubular member 332. Gas is ionized as it comes into contact with portions of the active and return electrodes 220, 222 contained within the non-conductive hollow tubular member 332 and the ionized gas is then projected through the opening 336 of the non-conductive hollow tubular member 332 that is located closest to the sharp cutting end 218 of the ultrapolar electrosurgery blade 200. Wires 180 connect first conductive hollow tube 120 and second conductive hollow tube 122 to a circuit board (not shown) within the handpiece member 112 which is in turn connected to a power source via a power cord 184. Selection buttons 188 on handpiece member 112 are used to activate cutting and/or coagulation.

The above description of exemplary embodiments of the invention shows various exemplary embodiments of the invention. These exemplary embodiments and modes are described and shown in sufficient detail to enable those skilled in the art to practice the invention and are not intended to limit the scope, applicability, or configuration of the invention in any way. Rather, the disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. An ultrapolar telescopic electrosurgery pencil with argon beam capability comprising:

a handpiece member with a channel having first and second ends;
a first conductive hollow tube contained within the channel;
a second conductive hollow tube contained within the channel;
a hollow telescopic member having first and second ends wherein the second end of the hollow telescopic member is contained within the handpiece member;
a third conductive hollow tube having a smaller diameter than the first conductive hollow tube, said third conductive hollow tube being contained within the hollow telescopic member and at least a portion of the first conductive hollow tube;
a conductive cylindrical member contained within the hollow telescopic member and at least a portion of the second conductive hollow tube;
an ultrapolar electrosurgery blade positioned within the first end of the hollow telescopic member where the ultrapolar electrosurgery blade includes a non-conductive blade having opposing planar sides, a sharp cutting end, and both an active contact and a return contact on each of the opposing planar sides of the non-conductive blade wherein the active contacts are connected to the third conductive hollow tube and the return contacts are connected to the conductive cylindrical member; and
a non-conductive hollow tubular member positioned on the ultrapolar electrosurgery blade such that it covers at least a portion of an active contact on one opposing planar side of the non-conductive blade and at least a portion of a return contact on the other opposing planar side of the non-conductive blade.

2. The ultrapolar telescopic electrosurgery pencil of claim 1 further comprising at least one support member for retaining the first conductive hollow tube and the second conductive hollow tube within the channel of the handpiece.

3. The ultrapolar telescopic electrosurgery pencil of claim 1 further comprising at least one support member for retaining the third conductive hollow tube and the conductive cylindrical member within the hollow telescopic member.

4. The ultrapolar telescopic electrosurgery pencil of claim 1 further comprising a non-conductive shelf support for supporting the non-conductive hollow tubular member when positioned on the non-conductive blade.

5. The ultrapolar telescopic electrosurgery pencil of claim 1 further comprising a rotating member connected to the second end of the handpiece member.

6. The ultrapolar telescopic electrosurgery pencil of claim 1 further comprising a second non-conductive hollow tubular member positioned between, and connected to, the non-conductive hollow tubular member and the third conductive hollow tube.

7. The ultrapolar telescopic electrosurgery pencil of claim 1 wherein the non-conductive hollow tubular member comprises a ceramic.

8. The ultrapolar telescopic electrosurgery pencil of claim 1 wherein the non-conductive blade comprises a ceramic.

9. The ultrapolar telescopic electrosurgery pencil of claim 1 wherein the non-conductive hollow tubular member includes a slot which fits over at least a portion of a top of the non-conductive blade.

10. The ultrapolar telescopic electrosurgery pencil of claim 9 wherein the non-conductive tubular member further includes an opening located above the slot on each end of the non-conductive tubular member.

11. The ultrapolar telescopic electrosurgery pencil of claim 6 wherein the non-conductive hollow tubular member is positioned outside of the first end of the hollow telescopic member.

12. The ultrapolar telescopic electrosurgery pencil of claim 1 wherein the second conductive hollow tube comprises an insulator on its outer surface.

13. The ultrapolar telescopic electrosurgery pencil of claim 1 wherein the first conductive hollow tube comprises an insulator on its outer surface.

* * * * *